United States Patent
Hsieh et al.

(10) Patent No.: US 8,525,991 B2
(45) Date of Patent: Sep. 3, 2013

(54) METHOD TO MEASURE PARTICLE MOBILITY IN SOLUTION WITH SCATTERED AND UNSCATTERED LIGHT

(71) Applicant: Wyatt Technology Corporation, Santa Barbara, CA (US)

(72) Inventors: Hung-Te Hsieh, Santa Barbara, CA (US); Steven P. Trainoff, Goleta, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 13/783,160

(22) Filed: Mar. 1, 2013

(65) Prior Publication Data
US 2013/0182254 A1    Jul. 18, 2013

Related U.S. Application Data

(62) Division of application No. 12/782,682, filed on May 18, 2010, now Pat. No. 8,441,638.

(60) Provisional application No. 61/308,781, filed on Feb. 26, 2010.

(51) Int. Cl.
*G01N 21/00*    (2006.01)

(52) U.S. Cl.
USPC .......................................... 356/344; 356/450

(58) Field of Classification Search
USPC ................. 356/344, 450–521, 335–343, 28.5
See application file for complete search history.

(56) References Cited

U.S. PATENT DOCUMENTS

| | | | | |
|---|---|---|---|---|
| 3,532,427 A | * | 10/1970 | Huffaker et al. | 356/28 |
| 3,732,014 A | * | 5/1973 | Uzgiris | 356/336 |
| 3,825,346 A | * | 7/1974 | Rizzo | 356/28.5 |
| 4,097,153 A | | 6/1978 | DeRemigis | |

(Continued)

FOREIGN PATENT DOCUMENTS
WO    WO85/04486 A1    10/1985

OTHER PUBLICATIONS

E.E.Uzgiris, "Laser Doppler methods in electrophoresis," Prog. Surf. Sci., 1981, pp. 53-164, vol. 10., Pergamon Press Ltd., Great Britain.

(Continued)

*Primary Examiner* — Tarifur Chowdhury
*Assistant Examiner* — Michael P Lapage
(74) *Attorney, Agent, or Firm* — Philip J. Wyatt; David N. Villalpando

(57) ABSTRACT

A method is disclosed for measurement of the electrophoretic mobility of particles in solution. A sample is placed in a cell containing two electrodes that apply an alternating electric field. A monochromatic light beam passes through the sample. Light scattered by the particles, along with the unscattered beam, is collected and collimated as it exits the cell. This beam is combined in free space with a phase modulated reference beam. The interference forms a frequency modulated speckle pattern, which is detected by a photodetector array. Each array element collects a narrow range of well-defined scattering angles. The signal from each is demodulated to provide a first-principle measurement of the electrophoretic mobility of the scattering particles. Each detector element provides a simultaneous independent measurement increasing the amount of information which results in increased sensitivity, extending mobility measurements to particles below one nanometer while reducing the required concentration and electric field.

19 Claims, 11 Drawing Sheets

(56) References Cited

U.S. PATENT DOCUMENTS

| | | | | |
|---|---|---|---|---|
| 5,171,534 A | * | 12/1992 | Smith et al. | 204/612 |
| 5,215,883 A | * | 6/1993 | Chu | 204/452 |
| 5,600,444 A | * | 2/1997 | Tong | 356/432 |
| 2004/0251134 A1 | * | 12/2004 | Sekiwa et al. | 204/450 |
| 2006/0114467 A1 | | 6/2006 | Nicoli et al. | |

OTHER PUBLICATIONS

J. F. Miller, K Schatzel, B. Vincent, "The determination of very small electrophoretic mobilities in polar and nonpolar colloidal dispersions using phase analysis light scattering," J. Colloid and Interface Science, 1991, pp. 532-554, vol. 143, No. 2, Academic Press, Inc., USA.

Malvern Instruments Ltd., "Zetasizer nano zs," promotional product literature, 2009, pp. 1-8, Malvern Instruments Ltd, United Kingdom.

Brookhaven Instruments Corporation, "Brookhaven ZetaPALS Zeta Potential and Particle Size Analyzer," promotional product literature, pp. 1-2, Brookhaven Instruments Corporation, USA.

R. G. W. Brown, "Homodyne optical fiber dynamic light scattering," Applied Optics, 2001, pp. 4004-4010, vol. 40, No. 24, Optical Society of America, USA.

Brookhaven Instruments Corporation, "Brookhaven ZetaPLUS Zeta Potential and Particle Size Analyzer," promotional product literature, pp. 1-2, Brookhaven Instruments Corporation, USA.

W. W. Tscharnuter, "Mobility measurements by phase analysis," Applied Optics, 2001, pp. 3995-4003, vol. 40, No. 24, Optical Society of America, USA.

Beckman Coulter, "DelsaNano Zeta Potential and Submicron Particle Size Analyzer," web page, pp. 1-5, Beckman Colter, Inc., USA.

* cited by examiner

METHOD TO MEASURE PARTICLE MOBILITY IN SOLUTION WITH SCATTERED AND UNSCATTERED LIGHT

PRIORITY

This is a divisional of U.S. application Ser. No. 12/782,682 filed May 18, 2010, "Method and apparatus to measure particle mobility in solution," which claims priority to U.S. Provisional Application 61/308,781 filed Feb. 26, 2010, "Method and apparatus to measure particle mobility in solution."

BACKGROUND

The invention discloses an innovative method and apparatus by which the motion of charged particles in a solution subject to an applied electric field may be measured. Although the present invention will refer to macromolecules throughout much of its specification, the invention includes more generally all classes of small particles including emulsions, viruses, nanoparticles, liposomes, macro-ions and any other solution constituents whose size may lie between a half and a few thousand nanometers. Thus whenever the terms "molecule," "macromolecule," or "macro-ion" are used, it should be understood they include all of the aforementioned solution-borne objects.

The electrophoretic mobility is the directly measurable and most widely used quantity to characterize the charge of the molecules, or for that matter any other particles present, in such solutions. Once measured, the electrophoretic mobility can in turn be used to determine the effective charge, $Ze$, carried by such molecules as well as its so-called zeta potential $\zeta$. The interface between the group of ions tightly bound to the particle and those of the surrounding solution that do not move with the particle defines the hydrodynamic shear plane. The zeta potential represents the electrostatic potential existing at this shear plane. It is a basic objective of the present invention to provide an improved means by which the electrophoretic mobility, effective charge, and zeta potential of molecules and particles in solution may be measured.

Electrophoresis is the migration of macro-ions under the influence of an electric field. A steady-state electrophoretic velocity, $v_e$, attained by the migrating macro-ions is linearly proportional to the applied electric field. When a field is applied, the molecules' velocities are essentially always in equilibrium. One can measure the proportionality constant, in this case the electrophoretic mobility, by measuring the electrophoretic velocity and dividing by the applied electric field. An objective of the present invention is to provide an improved apparatus capable of measuring the electrophoretic velocity of particles in solution more accurately than has been possible heretofore.

Several techniques have been developed and are available for measuring mobilities. Among these techniques are the Moving Boundary Method, Microelectrophoresis, and light scattering methods such as heterodyne dynamic light scattering, DLS, laser Doppler electrophoresis, LDE, and phase analysis light scattering, PALS. The Moving Boundary Method employs a specialized cell to establish two sharp boundaries between the macromolecular solution and a buffer. The translation of the boundaries under the application of an electric field provides a quantitative means to determine mobilities. Microelectrophoresis is based on directly observing the electrophoretic motion of individual particles with magnifying optics. However, microelectrophoresis is limited to measurement of the mobilities of particles much larger than about 100 nm in radius. Light scattering techniques have also been developed for measuring electrophoresis. Light scattered from moving particles carries information relating to such motion and from which their electrophoretic mobility may be determined.

Consider now the most significant of these measurement techniques for the measurement of electrophoretic mobilities: PALS. A beam of monochromatic light, usually from a laser source, illuminates a sample of liquid borne particles exposed to an applied electric field. Some of the light they scatter is collected and combined with a fraction of the incident unscattered light. In other words, the scattered signal is combined coherently with the incident light to produce a heterodyned signal. Such combination of the two beams is generally achieved using a single mode fiber to insure good alignment between the two beams. This technique generates fringes with high contrast, but results in a combined beam of relatively low intensity as a large fraction of the energy of each component beam is lost to modes not supported by the fiber. It is another objective of the present invention to combine such beams in free space producing a combined coherent beam of far greater energy and a correspondingly simplified detector system.

In order to measure the fluctuations of the combined beams and derive therefrom measurement of the electrophoretic mobility of the scattering particles, one of the combining beams is directed to reflect first from an oscillating mirror. This causes the detected fringes to aquire an intensity modulation, even in the absence of electrophoretic motion. The electrophoretic motion that results from the application the applied field produces a frequency shift permitting, thereby, an unequivocal determination of the sign of the mobility. However, practical considerations, such as those discussed by Robert G. W. Brown in "Homodyne Optical Fiber Dynamic Light Scattering," *Appl. Opt.* 40, 4004-4010 (2001), require the relative intensities of the two combined beams must be adjusted so that the ratio of the two is less than about 30. Another objective of the present invention is to remove the need to adjust the beams' relative intensities allowing such ratios to be greater than even 100:1 in order to take advantage of the effect known as coherent amplification, which will be described in greater detail in the section entitled Detailed Description of the Invention.

Because the combined beam intensity ratios of the traditional PALS measurement are restricted to a relatively small range, the detection of the signals produced thereby requires use of a photomultiplier, PMT, or an avalanche photodiode, APD. Such detectors are expensive and can be severely damaged or even destroyed by their inadvertent exposure to ambient room light or other extraneous sources. Another important objective of this invention is to eliminate these expensive components while at the same time providing detection means that cannot be damaged by extraneous light sources. Because PMT and APD devices have very limited dynamic ranges, the light intensity and the ratio of the two beams must be continually adjusted to keep the detector within their linear ranges. Alternatively one must correct of the effects of the nonlinearity. An objective of this invention is to incorporate a detection means with a wide linear response so that such adjustments and modeling are unnecessary.

It is another objective of this invention to measure the mobility of molecular species rapidly and without damage to the molecules being measured. A further and particularly important objective of this invention is to measure the mobility of molecules whose effective size is well below the PALS limit of about 5 nm. Still another objective of this invention is to increase the linear range of measurements possible to extend to lower concentration and size.

A BRIEF DESCRIPTION OF THE INVENTION

This innovative implementation of the PALS technique begins conventionally with a coherent beam of laser light being split to produce two beams, a reference beam and a sample beam. The reference beam is directed to a modulator that impresses upon it a time varying phase modulation. This beam is then expanded and shaped so that it fully illuminates a detector array. The sample beam is focused into and passes through a cell containing a fluid sample comprising a suspension of molecules whose mobility is to be measured. Electrodes within the cell apply a time varying electric field to the illuminated sample. The transmitted sample beam, along with a portion of the light scattered by the sample, which now contains information about the motion of the molecules, are collimated by a lens. This sample beam is combined with the reference beam to form an interference speckle pattern on the detector array. The array is chosen so that each element covers one or more coherence areas of the speckle pattern and covers a narrow range of scattering angles determined by the focal length of the collimating lens. Since the reference beam is phase modulated, each detector element records a time varying signal with a frequency set by the phase modulator. The electronic signal from each detector element is amplified and filtered by a band pass filter around this frequency. One element on the array, the forward monitor, detects interference of the unscattered sample beam and the reference beam. The forward monitor measures the exact phase modulation that was impressed upon the reference beam. This signal is then used to demodulate the signals corresponding to the different scattering angles. The phase difference between the forward monitor and each detector determines the accumulated optical phase, and thereby, the mobility of the sample. The most important benefit conferred by this measurement technique is that each detector element provides an independent, simultaneous measurement. Since the precision of the mobility determination improves with the number of detectors used, an array with a large number of elements is preferred. Therefore, the technique is referred to as massively parallel phase analysis light scattering, MP-PALS. By averaging a number of elements the time required to achieve a specified precision decreases inversely as the number of elements, enabling the measurement of very small particles such as proteins. In addition, the reduced measurement time associated with MP-PALS decreases damage to fragile biological samples while minimizing electrochemical degradation of the electrodes.

A BRIEF DESCRIPTION OF THE DRAWINGS

FIG. 1 shows a phase diagram for light scattering. An electric field E along the x-axis is applied to drive electrophoresis.

FIG. 2 displays the measured optical phase due to (a) particle diffusion alone, (b) electrophoresis and diffusion, and (c) electrophoresis and diffusion averaged over multiple cycles of the applied electric field demonstrating that the electrophoretic component dominates, while the diffusional component is negligible. The sample is NIST standard reference material, SRM 1980, for electrophoretic mobility.

Figure 1:
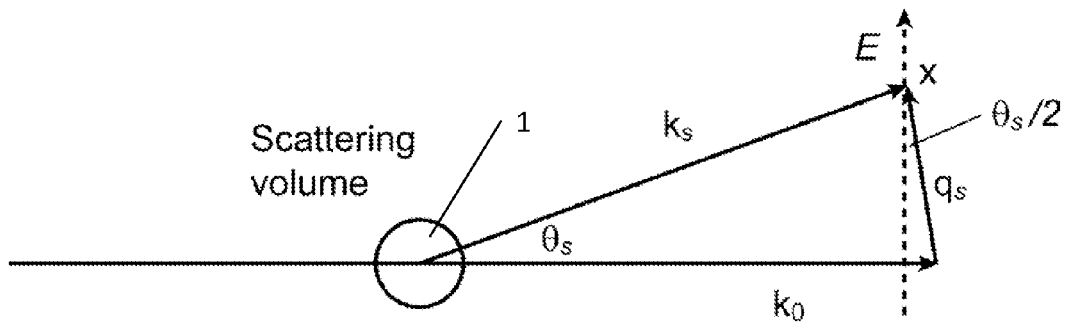

FIG. 7 displays the measured optical phase due to (a) particle diffusion alone, (b) electrophoresis and diffusion, and (c) electrophoresis and diffusion averaged over multiple cycles of the applied electric field demonstrating that the electrophoretic component dominates, while the diffusional component is negligible. The sample is 1.0 mg/ml bovine serum albumin in 10 mM NaCl, 1 mM phosphate buffer titrated with phosphoric acid to pH 3.4. The measured mobility is +2.26 µm·cm/V·sec, in good agreement with the value measured by capillary electrophoresis as reported by Menon and Zydney in "Measurement of Protein Charge and Ion Binding Using Capillary Electrophoresis," (*Anal. Chem.*, V 70, pp 1581-1584 (1998)).

A DETAILED DESCRIPTION OF THE INVENTION

Electrophoresis is the migration of macro-ions under the influence of an electric field. For field strengths less than about 200 V/cm, the steady-state electrophoretic velocity, $v_e$, imparted to the migrating macro-ions is linearly proportional to the applied electric field, E, i.e.

$$v_e = \mu E \quad (1)$$

where µ is the electrophoretic mobility, or the velocity per unit electric field. The time scale to reach a steady-state electrophoretic velocity is roughly m/f, where m is the mass of the macro-ion, the associated frictional force f is $6\pi\eta r_h$, $\eta$ is the solvent dynamic viscosity, and $r_h$ is the macro ion's hydrodynamic radius. For example, a molecule of bovine serum albumin, BSA, in an aqueous solution has m/f approximately 0.2 nsec. Thus, when a field is applied, the molecular velocities are effectively always in equilibrium. One can then measure the electrophoretic mobility by measuring the electrophoretic velocity and dividing by the applied electric field.

Several relationships have been derived that relate µ, Ze and ζ, but none of them is rigorous enough to be applicable under all circumstances. Various approximations and parameters such as Debye length, solution ionic strength, dielectric constant, viscosity, particle size, and macro-ion surface conduction all contribute to the complexity. Furthermore, non-idealities suggest that obtaining an exact analytical expression between µ and ζ is a formidable, if not impossible, task. One such non-ideality is called the electrophoretic effect, described by C. Tanford in *Physical Chemistry of Macromolecules*, whereby macro-ions/particles are necessarily surrounded by low-molar-mass counter-ions and co-ions, usually provided by the electrolyte. An excess of counter-ions exist in the vicinity of each of the macro-ions/particles. The electric field that drives the macro-ions will also act on these counter-ions, in the opposite direction. The moving, solvated counter-ions drag the solvent along with them and the solvent in turn acts on the macro-ions. The net effect is a secondary force that retards the movement of macro-ions. Another important non-ideality is ion relaxation where perturbation from equilibrium of the distribution of co-ions and counter-ions around the macro-ions arises from the very electric field that drives the movement of the macro-ions.

Several techniques have been developed for measuring mobilities. One of the earliest is called The *Moving boundary method* as described by R. A. Alberty in "An Introduction to Electrophoresis," in *J. Chem. Educ.*, 25, 426, 619 (1948). It utilizes a U-shaped Tiselius cell to establish two sharp boundaries between the macromolecular solution and an appropriate buffer. The macromolecular solution is usually dialyzed against the buffer prior to measurement. The translation of the (diffusion-broadened) boundaries under the application of an electric field provides a quantitative means to determine mobilities. Although implementation of the moving boundary method has contributed much to the knowledge of proteins and colloidal suspensions, it is associated with many experimental difficulties such as joule heating, electro-osmosis, dissimilar ascending and descending limbs, and the inevitable changes of buffer ion concentration across the boundaries leading to changes in pH and the macro-ion mobility. This is discussed by V. P. Dole in *J. Am. Chem. Soc.*, 67, 1119 (1945).

Another technique, developed specifically for very large particles, is microelectrophoresis based on the direct observation of the electrophoretic motion of individual particles with suitable magnifying optics. This was described by A. V. Delgado et. al. in their paper "Measurement and Interpretation of Electrokinetic Phenomena" in *J. Colloid Interface Sci.*, 309, 203 (2007). Nevertheless, the technique is limited by its optical resolution and cannot measure mobilities of particles much smaller than 100 nm in radius. Another disadvantage is that only a limited number of particles are measured, so the technique suffers from poor statistical accuracy. In addition, there is a selection bias based on how the particles are identified and tracked. The measurements usually take minutes or even hours to complete. As a result, joule heating, sample degradation, and electro-osmosis can present serious challenges.

Since the early 1970s, various light scattering techniques have been developed for measuring electrophoresis. Light scattered from moving particles is Doppler-shifted and carries information on their movement. FIG. 1 shows a light scattering phase diagram where the incident light is scattered by particles within the scattering volume 1 into a new direction with scattering angle $\theta_s$. The scattering vector defined as $q_s = k_s - k_0$, represents the difference between the wave vectors of the scattered and incident light. The direction is shown in FIG. 1, and the magnitude is $|q_s| = 4\pi n \sin(\theta_s/2)/\lambda$, where n is the refractive index of the solution and $\lambda$ is the wavelength of the light in vacuum. The electric field E along the x-axis results in an electrophoretic velocity $v_e = \mu E$. The optical phase $\phi_s$ of the scattered light is related to the positions of the scattering particles. Considering only the electrophoretic movement, the optical phase difference between time 0 and $\Delta t$ later is $\Delta \phi_s = q_s \cdot v_e \Delta t$, where $v_e \Delta t$ is the displacement of the particles due to electrophoresis. After some straightforward algebraic operations, the Doppler shift $\omega_s = d\phi_s/dt = \mu \cdot 2\pi n \cdot \sin(\theta_s) E/\lambda$ may be obtained. In general, the movement of particles can be collective (due to fluid flow, electrophoresis etc.) and diffusional (due to Brownian motion). The diffusional component, being stochastic in nature, averages to zero over time and the collective component can be revealed if enough measurement information is available to average out the diffusional component to zero. If one measures the average optical phase shift per unit time $d\bar{\phi}_s/dt$ $d\bar{\phi}_s/dt$ due to the applied electric field, the electrophoretic mobility $\mu$ may be determined.

Figure 2:
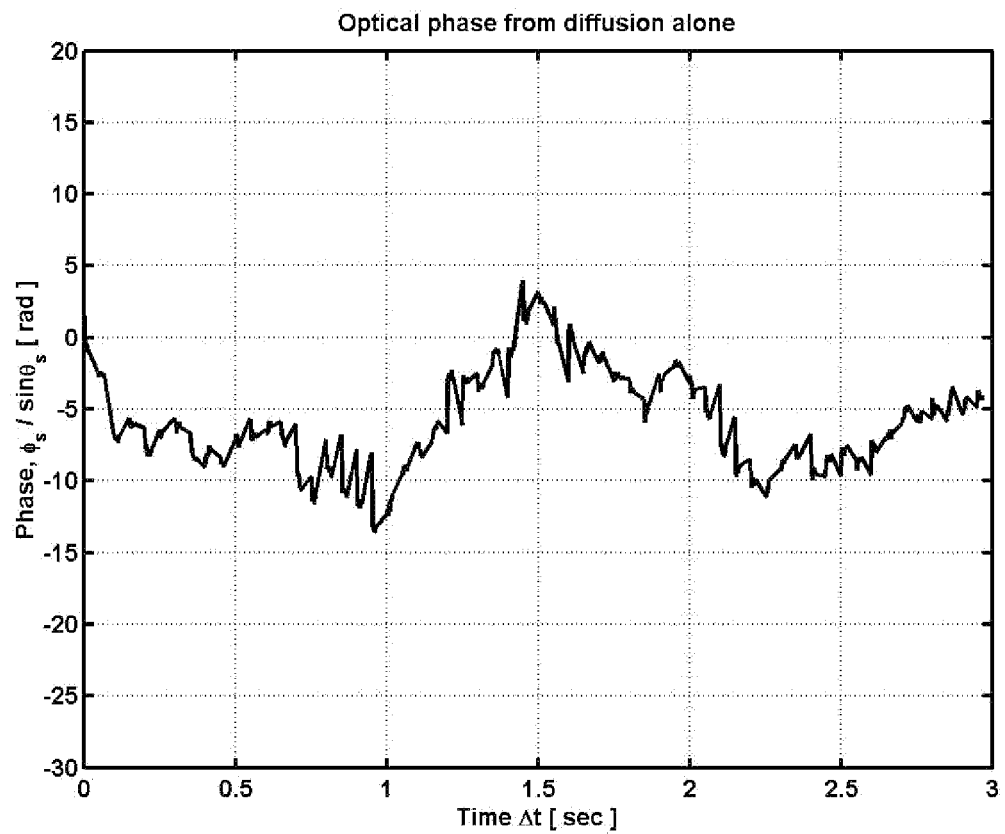
Figure 2:
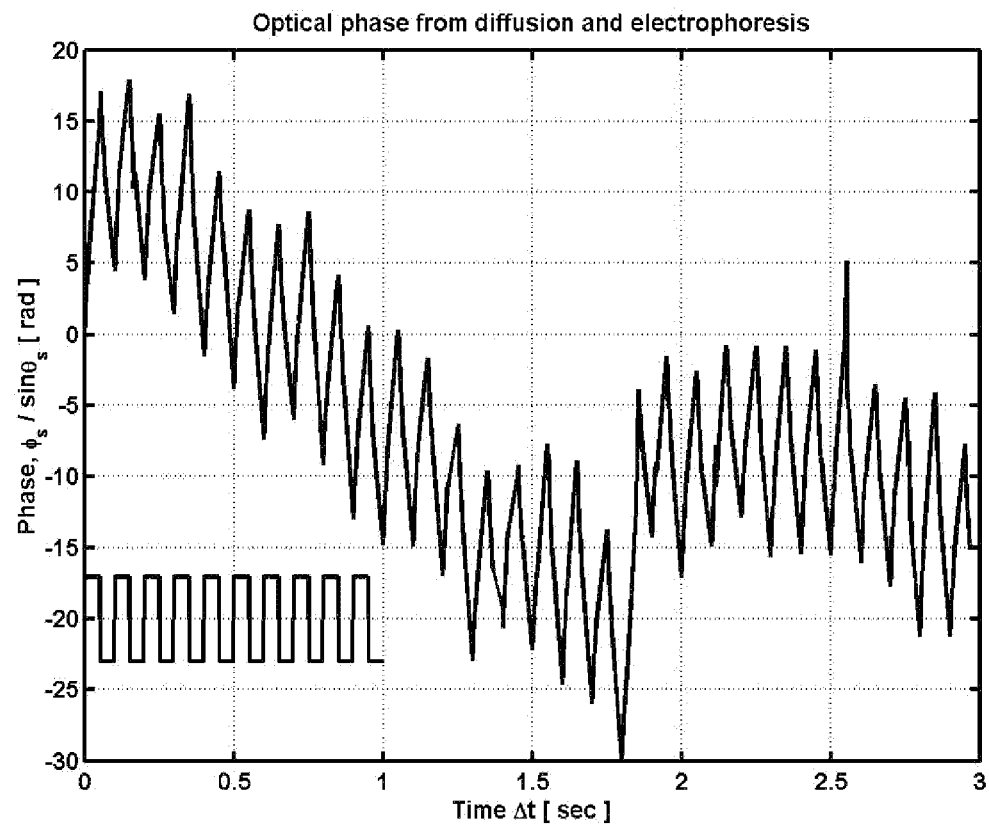
Figure 2:
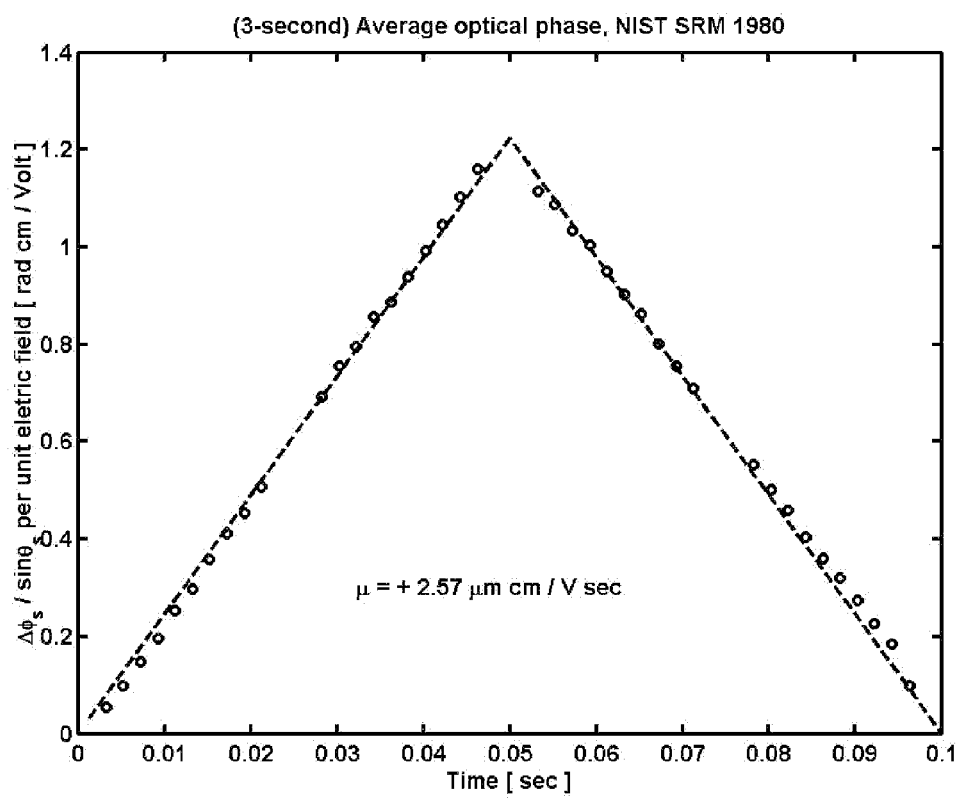

FIG. 2 illustrates how the optical phase associated with particle diffusion averages out to zero given enough measurement time. FIG. 2(a) shows the measured optical phase due to particle diffusion alone. A phase measurement is acquired every 2 milliseconds and normalized to sin $\theta_s$. The sample is the electrophoretic mobility standard reference material, SRM 1980, certified by the National Institute of Standards & Technology (NIST). It consists of acicular particles with an average dimension of 60 nm×20 nm as determined from electron microscopy. As is seen, this diffusional component is indeed random, and the corresponding phase wandering due to particle diffusion averages out to zero on the order of a few seconds. According to the Stokes-Einstein equation, the diffusion constant is inversely proportional to the hydrodynamic radius, therefore the smaller the particle, the longer it takes to average out the diffusional component. FIG. 2(b) graphs the measured optical phase when a 10 Hz, square-wave electric field with a magnitude of 18 V/cm is applied to drive the electrophoresis. The scaled and offset electric field is plotted below the optical phase for visual reference. Here the optical phase consists of both an electrophoretic and a diffusional component. As is clearly seen, the electrophoretic component reverses its direction whenever the electric field switches polarity, while the diffusional component remains independent of the electric field and proceeds randomly. In FIG. 2(c), the optical phase change per unit electric field is averaged over multiple cycles of the electric field and then fitted to a line for both the positive and negative sections of the electric field. Since the diffusional component averages out within several seconds, the electrophoretic mobility is readily obtained from the slopes of the fitted lines. The mobility of SRM 1980 is calculated to be +2.57 µm·cm/V·sec, well within the uncertainty of the NIST certified value, 2.53±0.12 µm·cm/V·sec. The mobility is accurately determined in less than three seconds. This measurement was performed with a laser operating at 660 nm, but any wavelength may be used.

In general, DLS measurements may be made in two different manners: homodyne and heterodyne. The terms heterodyne and heterodyne are often used inconsistently in the literature. For the purposes of this disclosure, we define them as follows: i) the homodyne mode wherein only light scattered from particles themselves is mixed, and ii) the heterodyne mode, where light scattered from the particles is mixed with some unscattered light often referred to as the local oscillator. To appreciate the distinctions between these two modes, we consider the photocurrent i(t) generated at the detector:

$$i(t) = \Re \left| \sqrt{P_{LO}} \, e^{i\omega t} + \sum_{j=1}^{N} \sqrt{P_O} \, e^{i\omega t} e^{i\varphi_j(t)} \right|^2,$$

$i(t) = \Re |\sqrt{P_{LO}} e^{i\Phi x} + \Sigma_{j=1}^{N} \sqrt{P_0} e^{i\Phi x} e^{i\Phi j(t)}|^2$ where $\Re$ is the detector responsivity, $\omega$ is the laser angular frequency, $P_{LO}$ is the local oscillator power, $P_0$ is the power of the scattered light from each of the N particles in the scattering volume, and $\omega_j(t)$ is the phase of the light scattered by the $j^{th}$ particle. Without loss of generality, we have assumed that all particles scatter with equal efficiency, i.e., they have the same polarizability. The phase $\omega_j(t)$ is related to the position $x_j(t)$ of particle j by $\omega_j(t) = q_s \cdot x_j(t)$. Because both diffusional and electrophoretic motion contribute to $x_j(t)$, the following relationship results:

$$\phi_j(t) = q_s \cdot x_j(t) = q_s \cdot [x_{jD}(t) + v_c t] = \phi_{jD}(t) + \phi_c(t),$$

where $x_{jD}(t)$ and $\phi_{jD}(t) = q_s \cdot x_{jD}(t)$ are the displacement and phase components associated with the Brownian motion of the $j^{th}$ particle and $\phi_c(t) = q_s \cdot v_c t$ is the phase component due to the collective velocity $v_c$, which is common to all particles; note that $x_{jD}(0)$ represents the initial position of the $j^{th}$ particle. Expanding i(t), yields $$i(t) = \Re\left\{P_{LO} + NP_0 2\sqrt{P_{LO}P_0}\sum_{j=1}^{N}\cos[\varphi_{jD}(t)+\varphi_c(t)] + \right.$$

$$\left. 2P_0\sum_{j=2}^{N}\sum_{k=1}^{j-1}\cos[(\varphi_{jD}(t)+\varphi_c(t))-(\varphi_{kD}(t)+\varphi_c(t))]\right\}$$

In the homodyne mode there is no local oscillator, therefore $P_{LO}=0$ and we end up with $$i(t) = \Re\left\{NP_0 + 2P_0\sum_{j=2}^{N}\sum_{k=1}^{j-1}\cos[\varphi_{jD}(t)-\varphi_{kD}(t)]\right\}$$

Note that all of the collective phase components $\phi_c(t)$s cancel out in i(t) for homodyne detection. Measurements obtained at all times t have the information-carrying terms $\phi_{jD}(t)-\phi_{kD}(t) = q_s\cdot[x_{jD}(t)-x_{kD}(t)]$. It is now clear that dynamic light scattering, DLS, in the homodyne mode is insensitive to collective particle movement since only diffusional information is available. Thus homodyne DLS is suitable for measuring hydrodynamic radii even when a flow is present, but it cannot be used to measure electrophoretic mobilities.

On the other hand, signals obtained from heterodyne DLS contain the terms cos $[\phi_{jD}(t)+\phi_c(t)]$ and carry phase information of both collective and diffusional components. Therefore, in order to measure electrophoresis with light scattering, optical heterodyning is necessary as described by B. J. Berne and R. Pecora in *Dynamic Light Scattering with Applications to Chemistry, Biology and Physics* (John Wiley & Sons Inc. 79 [1976]). R. Ware and W. H. Flygare in *J. Colloid Interface Sci.* 39, 670 (1972), showed how DLS in the heterodyne mode was used to measure the mobility of bovine serum albumin molecules at 50 mg/ml in 4 mM NaCl solution.

Another method, laser Doppler electrophoresis (LDE) was described by E. E. Uzgiris, in *Prog. Surf. Sci.* 10, 53 (1981). LDE involves detecting light scattered from macro-ions moving within a stationary fringe pattern. In LDE, the direction of the driving electric field is almost always made perpendicular to the phase fronts of the fringes. The fringe pattern is generated by the interference of two light beams derived from the same laser to ensure a good contrast ratio. The spacing between adjacent light and dark fringes is known from the angle of intersection between the interfering laser beams. As electric field-driven macro-ions traverse the light and dark fringes, a photodetector picks up a sinusoidal signal from the scattered light and the electrophoretic velocity may be measured and mobility obtained from the frequency of the sinusoidal signal.

LDE has important advantages over the earlier techniques. It greatly reduces the volume of sample required for mobility measurement, to milliliters or less, because the fringe pattern can be generated within the space between electrodes that are only 1-2 mm apart. Since the electric field is the voltage difference between the electrodes divided by their spacing, the reduced electrode spacing decreases the magnitude of the voltage that must be applied to generate observable electrophoresis. In addition, a large number of macro-ions contribute to the detected signal and this produces statistically sound measurements. To avoid electrode polarization, whereby ions accumulate near the electrodes and shield the bulk from the applied field, an oscillating a. c. electric filed is preferable to a d. c. field. The frequency of the field reversal should be made much lower than the Doppler frequency and much higher than the reciprocal of the time it takes for electro-osmosis to develop. The characteristic time of the development of electro-osmosis is $d^2/v$, where d is the relevant linear dimension and v is the kinematic viscosity of the solution. For aqueous solutions at 20° C., v≈1.0 mm$^2$/sec and the time it takes for electro-osmosis to develop is about 1 sec for a 1-mm electrode gap. However, when it comes to measuring low-mobility species, those with a mobility smaller than about 0.1-0.5 μm·cm/V·sec, LDE cannot satisfy both conditions without applying excessively high voltages and running into problems such as profuse electrolysis and fluid convection. Another limitation of LDE is that both positive and negative electric fields produce the same optical signal, so the sign of the mobility cannot be determined.

To address the limitations of LDE, phase analysis light scattering (PALS) was developed in the late 1980's by J. F. Miller, K. Schatzel, and B. Vincent in their paper "The Determination of Very Small Electrophoretic Mobilities in Polar and Nonpolar Colloidal Dispersions Using Phase Analysis Light Scattering," (*J. Colloid Interface Sci.* 143, 532-554 [1991]). PALS is derived from LDE and the major distinction between the techniques is that in PALS a sweeping, instead of stationary, fringe pattern is established in the scattering volume. Such fringe patterns can be generated by phase-modulating one or both of the interfering laser beams. The adoption of a phase demodulation scheme and band pass filtering of the detected optical signal goes a long way towards electronic noise rejection. A sweeping fringe pattern not only obviates the necessity of macro-ions having to traverse a few light and dark fringes during a single electric field period but also enables the determination of the sign of mobility. Zero-mobility, and therefore stationary, particles give rise to a Doppler frequency equivalent to that of the sweeping fringes and macro-ions migrating in the same or opposite direction of the sweeping fringes produce a Doppler frequency lower or higher than that of the sweeping fringes.

In another variation of PALS, instead of interfering the two laser beams at the scattering volume, the second laser beam, the local oscillator, is mixed/heterodyned directly on the detectors with scattered light from the macro-ions and acts both as an optical amplifier and as a phase reference which is indispensable in measuring the electrophoretic velocity. The local oscillator is phase-modulated for the same reason as explained above. In this configuration, PALS is actually an interferometric method in which one arm is the modulated local oscillator and the other is the scattered light. As the incident laser beam goes straight through the sample, the sample volume can be further reduced. Another advantage of this configuration is that it allows simultaneous heterodyne and homodyne measurements since the homodyne signal can be measured before the scattered light is mixed with the local oscillator and the heterodyne is measured after the mixing.

Consider next the optical amplification afforded by the local oscillator and its implication for the system signal-to-noise ratio, SNR. As explained previously, the photocurrent generated at the detector is proportional to the absorbed optical power:

$$i(t)=\Re\ |\sqrt{P_{LO}}e^{i(\omega+\Delta\omega)t}+\sqrt{P_S}e^{i\omega t}e^{i\phi_s(t)}|^2,$$

$i(t)=\Re\ |\sqrt{P_{LO}}e^{i(\omega+\Delta\omega)t}+\sqrt{P_S}e^{i\omega t}e^{i\phi_s(t)}|^2$ where $\Delta\omega$ is the frequency shift due to the phase modulation of the local oscillator. The scattered light from all the particles in the scattering volume has been summed up to obtain the last term, where $P_S$ stands for the power of scattered light and $\phi_s(t)$ is the optical phase that carries the information of particle movement. Expanding i(t), yields $$i(t) = \Re\,(P_{LO} + P_s)\left\{1 + \frac{2\sqrt{P_{LO}P_s}}{P_{LO} + P_s}\cos[\Delta\omega t - \varphi_s(t)]\right\}.$$

The benefit of heterodyning is clearly seen in the cross term $2\sqrt{P_{LO}P_s}\cos[\Delta\omega t - \phi(t)]2\sqrt{P_{LO}P_s}\cos[\Delta\omega t - \phi_s(t)]$, where the relevant signal power is coherently amplified by the local oscillator. The associated mean-square shot noise current is $$\overline{i^2_{N,Shot}} = 2e[i_d + \Re\,(P_{LO} + P_s)]\Delta B = 2e\left[i_d + \frac{\eta_e e}{h\nu}(P_{LO} + P_s)\right]\Delta B,$$

$$\overline{i^2_{N,Shot}} = 2e[i_d + \Re\,(P_{LO} + P_s)]\Delta B = 2e\left[i_d + \frac{\eta_e e}{h\nu}(P_{LO} + P_s)\right]\Delta B$$

where e is the electron charge, $i_d$ stands for the average detector dark current, and $\Delta B$ is the system bandwidth determined by the electronics. The responsivity $\Re$ may be expressed as $\eta_e e/h\nu$, where $\eta_e$ is the detector quantum efficiency (~70% for both silicon photodiodes and APDs at wavelengths around 700 nm), h is Planck's constant, and v is the light frequency. The detected mean-square signal current becomes $$\overline{i^2_s} = 2\left(\frac{\eta_e e}{h\nu}\right)^2 P_{LO}P_s.$$

The signal-to-noise ratio is therefore given by $$SNR = \frac{2\left(\frac{\eta_e e}{h\nu}\right)^2 P_{LO}P_s}{2e\left[i_d + \frac{\eta_e e}{h\nu}(P_{LO} + P_s)\right]\Delta B + \frac{4kT}{R}\Delta B}.$$

Figure 3:
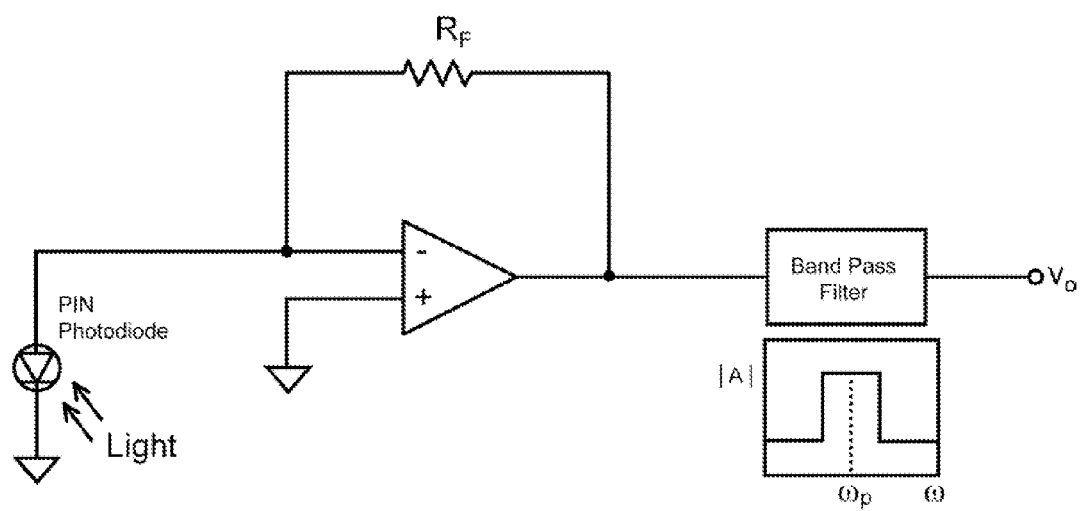
FIG. 3 represents a transimpedance amplifier that has a resistor $R_F$ in its feedback loop for current-to-voltage conversion and a subsequent band pass filter centered at $\omega_p$ for analog coupling.

The last term in the denominator represents the Johnson noise which comes from resistive components associated with the detection process, for example, the resistor $R_F$ in the feedback loop of a transimpedance amplifier as shown in FIG. 3. A band pass filter following the amplifier restricts the system bandwidth $\Delta B$ to minimize the noise terms. The center of the passband $\omega_p$ is set equal to the modulation frequency $\Delta\omega$ of the local oscillator for optimal performance.

The advantage of heterodyne detection is now clear: the SNR increases as the local oscillator power $P_{LO}$ grows until the shot noise term produced by the local oscillator completely dwarfs the other noise terms. At this limit, we have $$SNR = \frac{P_s}{\frac{h\nu}{\eta_e}\Delta B}.$$

The minimum detectable signal, defined as the signal input power leading to an output SNR of 1, is $$P_{s,min} = \frac{h\nu}{\eta_e}\Delta B.$$

This is the quantum limit of optical detection. For $\eta_e=1$, this power corresponds to a photon flux at a rate of one photon per $(\Delta B)^{-1}$ seconds, that is, one photon per resolution time of the system as explained by A. Yariv in *Optical Electronics in Modern Communications*, pages 423 et seq. Oxford University Press (1997).

Compared with LDE, PALS requires less time to perform a measurement and has greater sensitivity. PALS is also more suitable for measuring samples in non-polar solvents and low-mobility species, such as macro-ions close to their isoelectric points. A number of instruments currently on the market implement the PALS technique to measure the mobilities of macromolecules. Quantum-sensitive detectors such as PMTs and APDs are employed and mobility of macro-ions of size down to about 5 nm may be measured under exceptional conditions. The minimum measureable size of the macro-ions also depends on several other parameters such as the macroion molar mass, concentration, and the duration of the measurement. This makes PALS suitable for measuring larger particles, but not for biomolecules such as proteins, as most of these molecules are smaller than 5 nm. One of the objectives of the present invention is to overcome this size limitation, allowing the precise measurement of particles much smaller than those measureable by the methods previously discussed.

As refined a technique as PALS is, current implementations on the market have limitations. In these instruments, single photon counting APDs are the preferred choice of detectors due to their sensitivity and high quantum efficiency. However, the use of APDs, which are essentially wide-bandwidth "digital" detectors, forfeits the advantage of analog filtering for noise rejection afforded by PALS. To measure electrophoresis, the scattered and local oscillator light are collected by a fiber-lens module and the mixed signal is guided towards the APD for photo detection. The generally accepted rule-of-thumb is that the local oscillator must be approximately 30 times stronger than the scattered light signal for negligible line width distortion as reported, for example, by C. J. Oliver in the chapter titled "Correlation techniques," in *Photon Correlation and Light Beating Spectroscopy*, pp. 151-223, H. Z. Cummins and E. R. Pike, eds., Plenum, New York 1974. Because APDs have a limited dynamic range and become nonlinear at count rates >2 MHz, the intensity ratio between the local oscillator and the scattered light needs constant adjusting to maintain optimum sensitivity. If the ratio is too low, homodyne signal creeps into the measurement. If the ratio is too high, the APDs are driven into their nonlinear regime or saturated. Moreover, APDs are at least an order of magnitude more expensive than silicon PIN photodiodes and the associated commercial instruments are limited to a single detector channel, utilizing only a tiny fraction of the scattered light for mobility measurement.

This limitation proves unwieldy for measurements of small molecule mobilities at $r_h<5$ nm due to the more pronounced Brownian motion associated with them. Measurement times of minutes or even tens of minutes are required to average out the diffusional phase component. Thus the main reason why these instruments specify a minimum measurable size of 5 nm for electrophoretic mobilities is that in order to average out the diffusional components of smaller molecules, lengthier measurement times are required. Beyond the mere inconvenience and inefficiency of these long measurements, prolonged periods of measurement are often not feasible, especially when fragile samples are involved.

Advances in biotechnology have created even more challenges to this field. Formulation scientists are interested in learning of the stability of stored samples, e.g., recombinant therapeutic proteins. Protein mobility is a critically important indicator of stability: in general, the higher the mobility, the more superficially charged the proteins are, and electrostatic repulsion reduces the tendency to aggregate. The most interesting and most investigated proteins are those with molar masses less than ~200 kD and radii often far smaller than 5 nm. For example, IgG molecules have a molar mass of ~150 kD and a hydrodynamic radius of ~4.6 nm. Measuring the mobilities of these molecules is a daunting task with any of the instruments available at the time of this invention; the proteins near the electrodes are damaged before a consistent measurement is obtained. The situation worsens when the molecular size and/or the mobility become even smaller. In this size range, the macromolecules scatter far less light and the more active particle diffusion contributes to the uncertainty of measured displacement. As discussed by J. F. Miller, K. Schatzel, B. Vincent in their paper "The Determination of Very Small Electrophoretic Mobilities in Polar and Nonpolar Colloidal Dispersions Using Phase Analysis Light Scattering," *J. Colloid Interface Sci.* 143, 532-554 (1991), the relevant signal-to-noise ratio $SNR_D$ due to particle diffusion may be expressed as $SNR_D \propto \mu E(T/D)^{0.5}$, where T is the total measurement time and D is the particle translational diffusion coefficient. To increase $SNR_D$ for a given sample, we either must increase the applied electric field or make measurements over longer time periods. Unfortunately, both options have deleterious effects on the measured macromolecules and usually bring about sample degradation and plating onto the electrodes; this is especially true for 'finicky' and fragile protein like antibodies. To accomplish this measurement in a satisfactory manner, it is imperative to keep the measurement time as short as possible.

The inventive implementation of the MP-PALS technique disclosed herein solves this dilemma by performing multiple simultaneous measurements with an array of detectors. When scattered light impinges on a screen, as discussed by B. J. Berne and R. Pecora in their earlier cited text, a diffraction/speckle pattern is produced which depends, among other things, on the extent of the scattering volume; i.e., the intensity maxima and minima depend on the dimensions of the scattering volume. On any given point P on the screen, one could define a region near the point P such that the signals at all points within this region are partially coherent with that at P. This region is called the coherence area. A useful estimate of the coherence area for light scattering is $A_{coh} = \lambda^2/\Omega$, where $\Omega$ is the solid angle subtended by the scattering volume at the detector(s). As $\Omega$ grows smaller, $A_{coh}$ becomes larger. In the present inventive implementation, since each detector channel makes an independent measurement, N channels will reduce the measurement time by a factor of N. As long as the active area of each detector element is greater than or equal to the coherence area of the scattered light, the signals collected from different detector elements are truly independent. This parallelism is made possible by an innovative optical design that allows free space multiplexing of the interfering beams. The power of such parallelism is clearly demonstrated in FIG. 7.

Figure 7A:
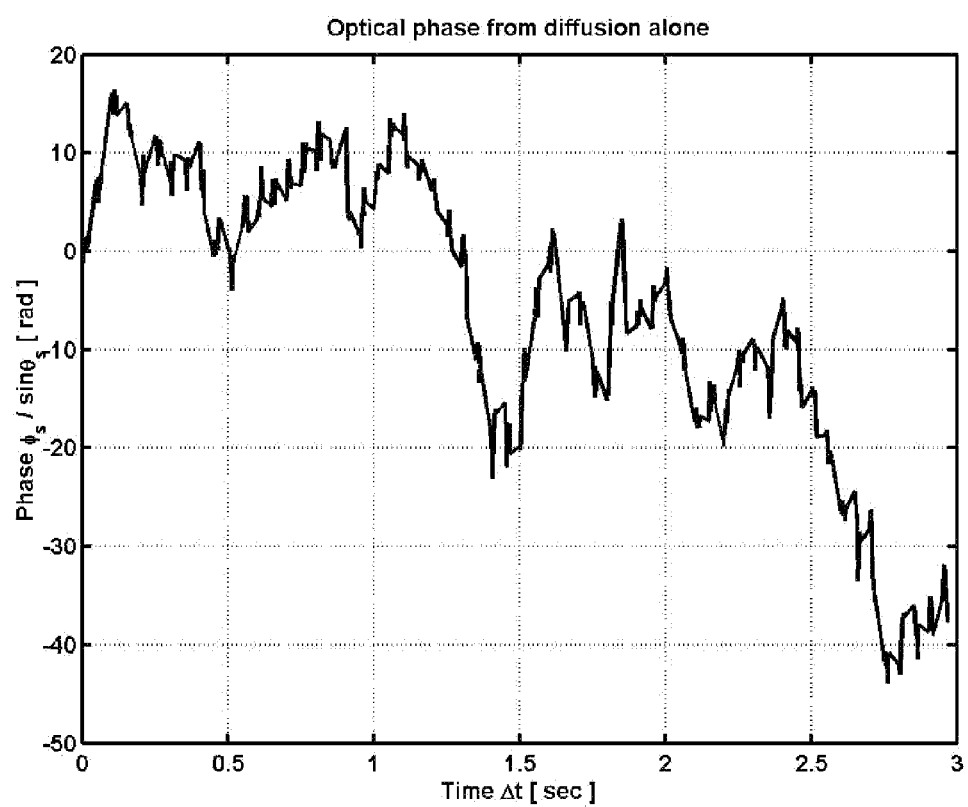
Figure 7B:
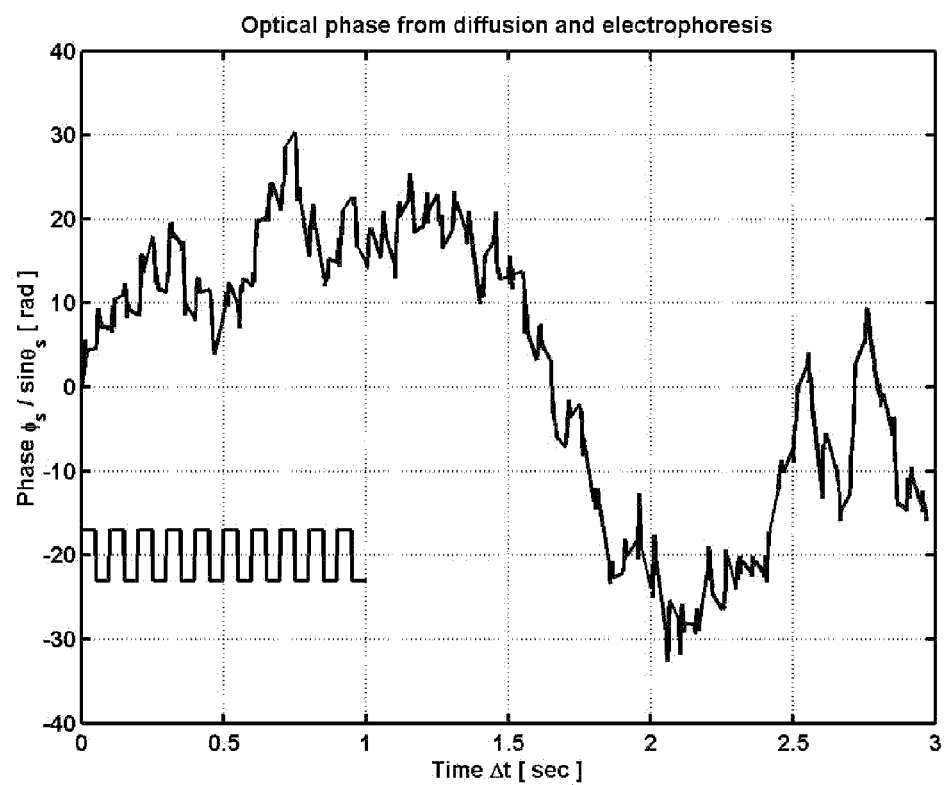
Figure 7C:
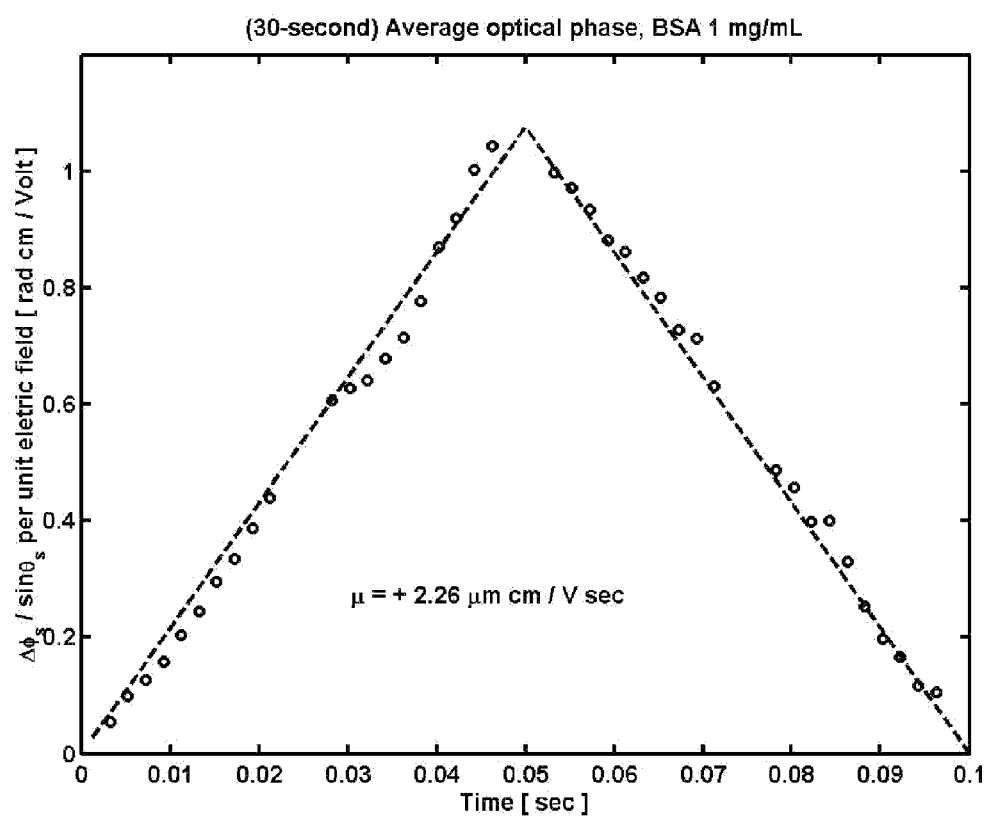

In FIG. 7 we present data from a small protein ($r_h$=3.5 nm), 1.0 mg/ml bovine serum albumin, BSA, in 10 mM NaCl, dissolved in a 1 mM phosphate buffer titrated with phosphoric acid to pH 3.4. FIG. 7(a) shows the phase accumulation due only to diffusion. Compared to the large particle shown in FIG. 2(a), the phase wander due to diffusion is much larger. FIG. 7(b) shows the phase accumulation with the oscillating electric field applied. For small particles the motion is masked by diffusion, and the data shown in FIGS. 7(a) and 7(b) look essentially the same. However, the massive parallelism of MP-PALS shown in FIG. 7(c) allows accurate measurement of the mobility of this small molecule. Such a measurement has not been possible prior to the invention of MP-PALS. This represents an improvement in sensitivity of at least an order of magnitude over existing PALS instruments.

All instruments that quantitatively measure the electrophoretic mobility of macro-ions or dispersed particles need to subject the particles of interest to an electric field of known magnitude and determine, from the application of this electric field, the speed at which the affected particles travel in the direction of the applied field. Referring to FIG. 1 and the earlier discussion, for instruments based on light scattering, some form of coherent interference is always necessary. One can establish an interference pattern that contains the scattering volume 1 and then measure the light intensity scattered from the moving macromolecules. Alternatively, the light scattered off the migrating macromolecules in the scattering volume 1 is mixed with a coherent local oscillator at a detector and the information-bearing optical phase is extracted. We implement the latter option because it allows not only for a narrower gap between field producing electrodes but also provides a more economical use of available light intensity.

Figure 4:
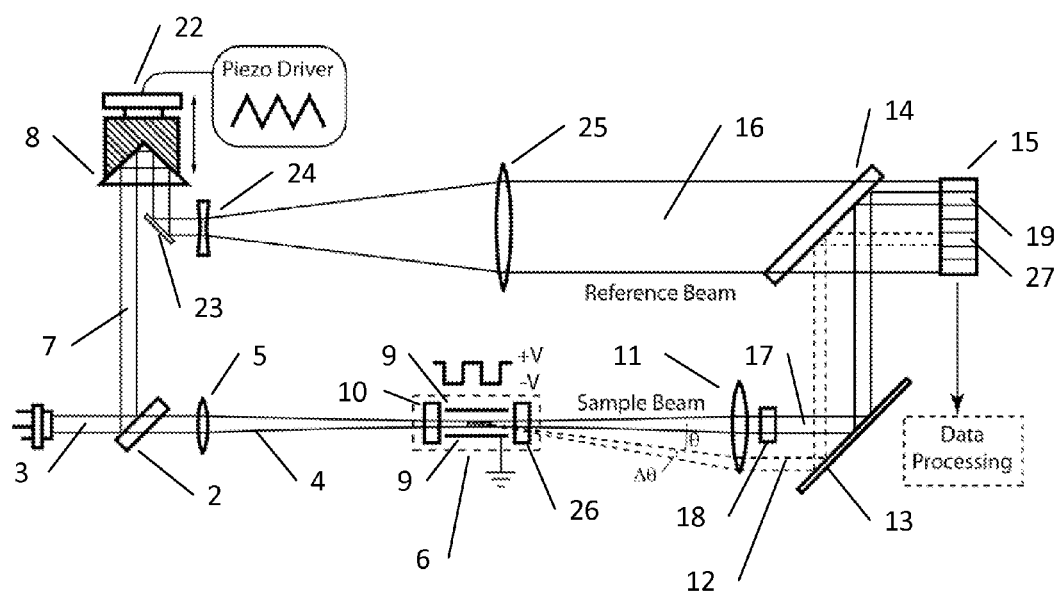
FIG. 4 shows the MP-PALS setup realized by free-space optics and a photo detector array.

FIG. 4 shows the inventive implementation of a PALS-based instrument that measures electrophoretic mobilities. A beamsplitter 2 splits a laser beam 3 into two beams: the sample beam 4 is focused by a lens 5 at the center of the sample cell 6 while the reference beam 7 is directed towards a prism 8.

The sample cell 6 is comprised of a chamber containing two electrodes 9 and sealed by the entrance window 10 and exit window 26 that permit the passage therethrough of the sample beam 4. The chamber is usually filled completely with sample solution. The absence of free surfaces deters the development of fluid convection and extends the range of sample ionic strength that may be used. For samples with higher ionic strengths, more current is expected to flow across the fluid-filled space between the electrodes, and fluid convection due to joule heating can eventually develop. Effects due to steady-state fluid convection can be accounted for in data analysis because the electrophoretic movement reverses direction whenever the applied field reverses polarity while the convective component is independent of the field polarity. The problem, however, is that if the cell is not temperature-regulated the heat released within the cell causes the convection to build up over time, and it fails to reach a steady state during the measurement. Varying fluid viscosity due to a changing temperature can also complicate mobility measurements. One embodiment of the present invention mitigates this problem by cooling the bottom of the cell and heating the top to develop an antagonistic temperature gradient and stabilizing the system against convection.

The built-in electrodes 9 serve three purposes: the regulation of cell/sample temperature, the measurement of sample conductivity $\sigma$, and the application of an electric field E to drive electrophoresis. The body of the cell must be electrically insulating and common electrical insulators (such as plastic) are typically thermal insulators as well and, therefore, are not suitable for temperature regulating the cell. Accordingly, the thermally conductive electrodes must be temperature regulated. This may be achieved by attaching thereon thermoelectric devices to heat or cool the contained sample as well as stabilize the cell/sample temperature while electric power is being dissipated in conducting samples. For mobility measurements, once the sample has reached the desired temperature, the conductivity $\sigma$ of the solution of interest is determined by applying a voltage pulse of known magnitude between the electrodes and measuring the resulting current, which is then compared with that of a conductivity standard such as, for example, potassium chloride, KCl. During measurements of electrophoretic mobilities, some combination of a voltage and a current source is applied across the electrodes to generate the electrophoresis-driving electric field E, which can be determined from the relationship $E=J/\sigma$; where J is the measured current density.

Note that J is measured in real-time and σ has been previously determined. The electrodes may be made of or coated with various conducting materials such as stainless steel, gold, platinum or palladium. The material of choice may be selected on the basis of its tarnish resistance and chemical compatibility with the sample of interest.

For conducting samples, the dissipated power per unit volume is E·J, or $\sigma|E|^2$. For high conductivity samples, a correspondingly high current is needed to generate a commensurate electric field. Therefore, the joule heating goes linearly with the sample conductivity. For example, a constant electric field 20 V/cm in a 10 ms/cm sample (~50 mM phosphate buffered saline) entails joule heating of the order of 1° C./sec in aqueous solutions. As σ increases, the measurement grows more vulnerable to fluid convection and a changing viscosity due to a rising temperature. Moreover, high currents may produce various deleterious effects on the electrodes as well as the molecules being measured. The key to overcome these adversities lies in a shorter measurement time and a well-designed cell that impedes the development of convection currents. In non-conducting samples, no current is passed between the electrodes, and the applied electric field is simply the voltage difference divided by the electrode spacing. No power is dissipated within the cell, and there is no concern for any thermal effect.

As the focused sample beam traverses the sample cell 6, a portion of the light is scattered from the particles undergoing electrophoresis. That fraction of the scattered light 12 that can leave the sample cell through exit window 10 along with the unscattered sample beam 17 are then collimated by condenser lens 11 to form a combined collimated sample beam whose unscattered component 17 may be attenuated by attenuator means 18 before combining with the collected scattered fraction to reflect from mirror means 13. These reflected components are then further reflected from beamsplitter means 14 to fall upon an array of detectors 15. The mirror 13 and beamsplitter 14 achieve co linearity between the collimated scattered sample beam with its unscattered component and the reference beam 16 for optimal optical mixing/heterodyning at the detector array 15. Each array element intercepts a solid angle of scattered light and a range of corresponding scattering vectors, which are determined by the focal length of the condenser lens 11 as well as the positions and dimensions of the array elements. The unscattered portion of the now collimated sample beam 17 has been attenuated as may be required before reflecting a portion thereof at the beamsplitter 14 to be incident upon a particular array element 19 that will serve as the sample beam monitor.

Figure 5:
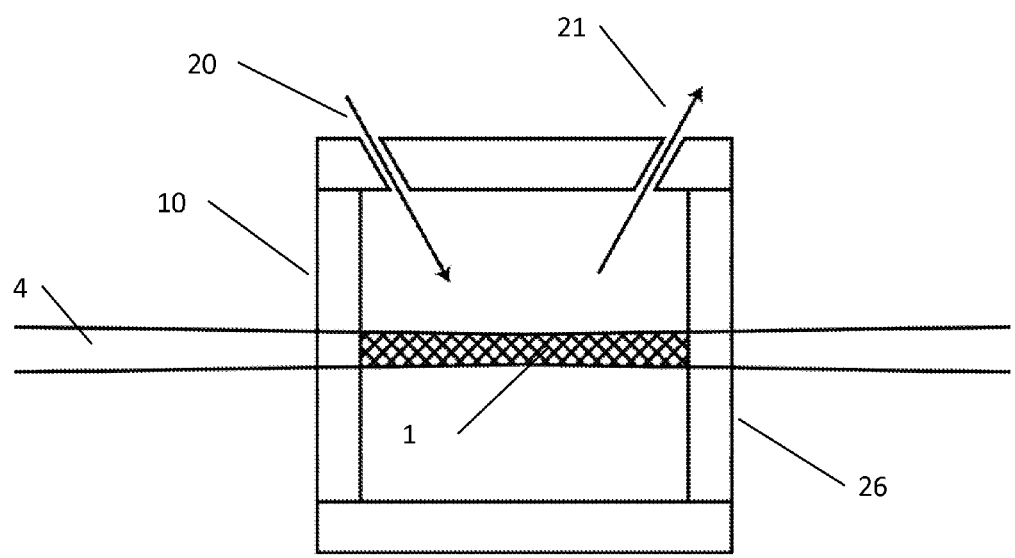
FIG. 5 is a detailed view of the measurement cell of one embodiment of the improved PALS system.

In a preferred embodiment of the invention, the internal region of the sample cell 6 is accessible to fluid flow through an inlet port 20 and an outlet port 21 as shown in FIG. 5, thus allowing the sample contained therein to be changed without the need to remove the cell.

Referring again to FIG. 4, the portion of the laser beam reflected from the beamsplitter 2 is retro-reflected successively by a right-angle prism 8. Since that prism 8 is used as a retro-reflector, its hypotenuse surface is anti-reflection coated to maximize light transmission. The prism 8 is continuously driven by a piezo-electric actuator 22 that imparts phase modulation parallel to the beam to facilitate the determination of the sign of measured electrophoretic mobilities and the rejection of electronic noise. The prism 8 serves two additional purposes:

1. Retro-reflection from the prism doubles the travel due to the piezo-electric actuator 22 and increases the amount of phase modulation for a given piezo-driving voltage. The same effect can also be achieved by replacing the prism 8 with two mirrors whose reflective surfaces are perpendicular to each other. This would eliminate the back reflection.
2. Compared with simple reflection of a single 45° mirror, retro-reflection eliminates the lateral beam displacement and avoids the associated amplitude modulation that would otherwise be received by the detectors 15.

After retro-reflection, the beam is redirected by a mirror 23 and then shaped by appropriate optics to serve as the reference beam 16, which is then transmitted through the beamsplitter 14 and falls onto the detector array 15, where it recombines collinearly with the reflected scattered sample beam fraction 12.

Figure 6:
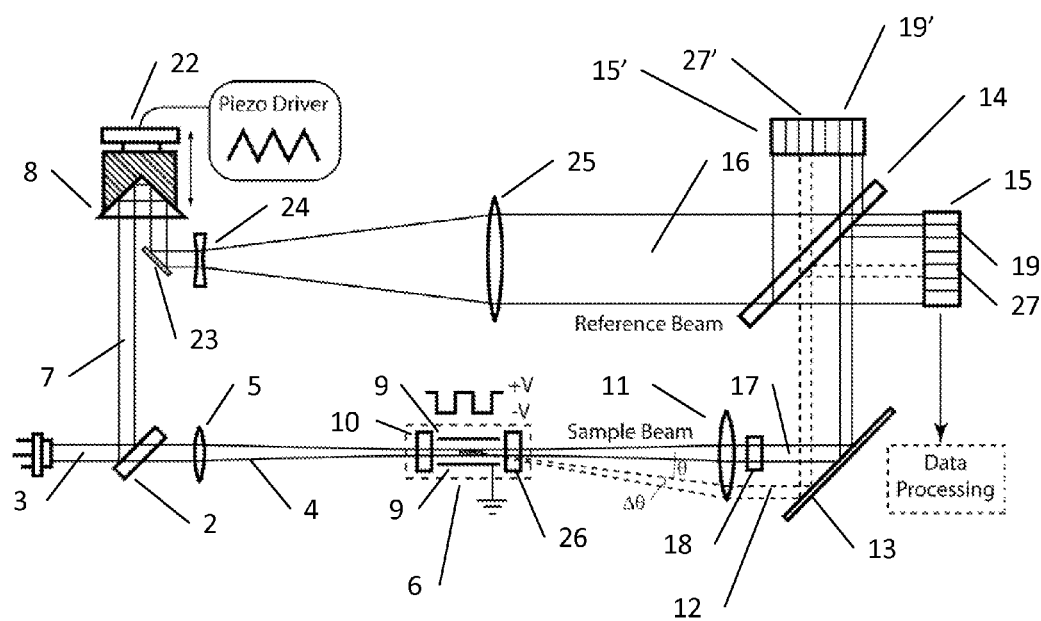
FIG. 6 illustrates an alternate implementation of the inventive MP-PALS setup shown in FIG. 4 in which two photo detector arrays are employed.

In FIG. 4 the reference beam transmitted through beam splitter 14 and the sample beam reflected by beam splitter 14 are measured by detector array 15. An alternative embodiment, shown in FIG. 6, includes a second photo detector array 15' which collects the reference beam reflected by beam splitter 14 and the sample beam transmitted by beam splitter 14. Detector arrays in positions 15 and 15' may be used simultaneously for improved averaging.

More generally, a two-dimensional array of detectors may be substituted for the linear array 15 for detection, and the shape of the reference beam 16 would be adjusted to illuminate effectively the array of photo detectors 15. For example, a Galilean telescope (with a proper magnification) could be used in reverse to obtain, thereby, a disk-shaped reference beam which then mixes with the also disk-shaped sample beam scattered fraction.

In the preferred embodiment of the invention, a linear detector array 15 is used and the beam shaping is accomplished with a pair of cylindrical lenses 24 and 25 to obtain an elongated reference beam 16. To cover adequately the linearly arranged elements, such an elongated reference beam makes the most economical use of available optical power.

Note that for the linear array detector 15, the collimated sample scattered fraction and reference beams must be both temporally and spatially coherent so that the interferometric-based measurement of mobility may be fully realized. The achieved coherence in both time and space are discussed below.

To achieve coherence in time, the coherence length of the light source should be much longer than the path length difference between the sample and reference beams; this is easily achieved by various coherent light sources, for example, gas lasers, solid-state lasers and frequency-stabilized semiconductor lasers. The selection of a specific coherent light source is dictated by the sample to which it is applied, e.g. for samples exhibiting absorption and/or fluorescence, and cost considerations, among other factors.

In this inventive PALS implementation, free space optics combined with silicon photodiode arrays are used for detection; the coherence in space (or wavefront phase-matching) is achieved by proper placement and orientation of the mirror 13 and the beamsplitter 14 to ensure collinear propagation of the collimated sample and reference beams. The maximum allowed angular deviation between the two beams $\theta_D$ is equal to $\lambda/2\pi w$ where w is the array element dimension and λ is the wavelength of the light in vacuum. This requires careful alignment of the optical system. All PALS instruments available on the market today attain spatial coherence differently. They use optical fibers for light collection. Such fibers transmit light in discrete "modes". Once the scattered light and local oscillator are coupled into the fibers, propagating modes are distilled from them and mutual spatial coherence is thus obtained. This is explained by Robert G. W. Brown in his paper "Homodyne Optical Fiber Dynamic Light Scattering,"

*Appl. Opt.* 40, 4004-4010 (2001). This is a inefficient process since non-propagating modes are lost through the fiber cladding. On the other hand, its ease of alignment is advantageous because the local oscillator beam and scattered light do not have to be precisely parallel. Unfortunately, in order to compensate for the low detection efficiency, quantum sensitive detectors such as APDs or PMTs with their restricted linearity and dynamic range are required.

From consideration of a higher information throughput alone for the measurement of mobility, the combination of free-space optics and a silicon photodiode array is far superior to the employment of light fibers and APDs or PMTs. The more challenging optical alignment may be achieved consistently with a well-constructed optical system and, once aligned, additional advantages are realized:

1. Scattered light incident on multiple array elements is heterodyned and detected simultaneously. Each array element performs an independent measurement and the measurement time required to average out the diffusional component is drastically reduced because the averaging takes place, not only in time but, also in space. Arrayed photodiodes easily lend themselves to such massive parallelism. In addition, multi-channel measurement with multiple APDs and light fibers would be prohibitively expensive.

2. This parallelism proves instrumental in reducing the minimum measurable particle size because the accompanying diffusional component is more readily eliminated. Minimum measurable particle size is extended to below 1 nm.

3. A shortened measurement time reduces the duration the sample molecules must be subjected to the electric current, helping to preserve thereby the integrity of samples as well as the system electrodes. This is especially important for precious and fragile samples of which proteins are an exemplar class.

4. In contrast to APDs and PMTs, photodiode arrays possess excellent linearity and a huge dynamic range (up to a factor of $10^{11}$). Taking advantage of the enormous dynamic range, one may use a very high intensity ratio of local oscillator to scattered light compared with systems that use APDs. This eliminates the need to adjust the intensity ratio between the two beams and makes shot-noise-limited performance possible. Furthermore, by modulating the phase of the local oscillator/reference beam, one may detect the signal with the modulating frequency chosen from an almost limitless variety of possibilities. This transforms the measurement of interest away from one that is DC-based and allows the use of analog coupling. In this manner, the noise bandwidth is greatly reduced by band pass filtering the signal about the modulation frequency. Moving away from DC also helps reduce the 1/f noise that is inherent in analog detectors.

5. The cost of components is much reduced. APDs are more expensive than entire photodiode arrays by more than an order of magnitude. Information throughput per unit cost in the inventive modification of PALS exceeds significantly that of systems/instruments utilizing light fibers and APDs or PMTs.

As will be evident to those skilled in the arts of light scattering, macromolecular characterization, and electrophoretic mobility measurements, there are many obvious variations of the methods and devices of our invention that do not depart from the fundamental elements that we have listed for their practice; all such variations are but obvious implementations of the invention described hereinbefore and are included by reference to our claims, which follow.

The invention claimed is:

1. A method to measure the electrophoretic mobility of particles in a sample solution comprising the steps of:

A) filling a sample cell with an aliquot of said sample solution, said sample cell comprising:
 a. a chamber to hold said sample aliquot,
 b. electrodes between which a voltage is applied across said sample aliquot contained therein, and
 c. optical windows in said chamber through which a light beam may passes;
B) providing means to generate a beam of coherent monochromatic light;
C) providing means to divide said beam of coherent monochromatic light into
 a. a sample beam that will pass through said sample cell unscattered, and a fraction of the sample beam light scattered from said particles in said sample aliquot leaves said sample cell, and
 b. a reference beam;
D) providing means to modulate the optical phase of said reference beam relative to the optical phase of said sample beam;
E) providing means to collect and collimate said sample beam leaving said sample cell unscattered and said fraction of said sample beam light scattered from said sample aliquot in said sample cell;
F) providing means to combine said reference beam with said collimated fraction of light scattered from said sample aliquot, forming thereby a third beam;
G) providing means to measure the light intensity values of said third beam at each of a plurality of photo detector elements placed in the path of said third beam;
H) providing means to convert said light intensity values measured at each photodetector element into digital representations;
J) processing said digital representations to obtain therefrom said electrophoretic mobility of said particles in said solution.

2. The method of claim 1 where said means to modulate the optical phase of said reference beam comprises a piezo-electric actuator that drives a retro-reflection means.

3. The method of claim 2 where said retro-reflection means is a right-angle prism.

4. The method of claim 3 wherein the hypotenuse surface of said right-angle prism is anti-reflection coated.

5. The method of claim 2 where said retro-reflection means is comprised of two mirrors whose reflective surfaces are perpendicular to each other.

6. The method of claim 1 where said photo detector elements are photodiodes.

7. The method of claim 1 where said plurality of photo detector elements is arranged in a one dimensional array.

8. The method of claim 1 where said plurality of photo detector elements is arranged in a two dimensional array.

9. The method of claim 1 wherein said sample cell is removable and filled prior to being placed into the path of said beam of coherent monochromatic light.

10. The method of claim 9 where said removable sample cell is disposable.

11. The method of claim 1 further comprising the step of providing means to collimate said reference beam prior to recombination with said sample beam.

12. The method of claim 11 where said means to collimate said reference beam comprises a diverging lens and a converging lens.

13. The method of claim 1 further comprising the step of providing means to focus said sample beam at the center of said sample cell.

14. The method of claim 1 further comprising the step of providing means to attenuate the non-scattered portion of said sample beam by means of a neutral density filter.

15. The method of claim 14 where said attenuated, non-scattered portion of said sample beam is incident on a single element of said plurality of photo detector elements providing thereby means to monitor said sample beam.

16. The method of claim 1 further comprising the step of providing temperature control means in contact with said electrodes enabling temperature control of said sample cell.

17. The method of claim 1 where said means to collect and collimate said sample beam leaving said sample cell unscattered and said fraction of said sample beam light scattered from said sample aliquot in said sample cell comprises an aspheric lens.

18. The method of claim 1 further comprising the step of providing optical means to shape said reference beam prior to recombination with said sample beam so as to allow for optimal utilization of said plurality of photo detector elements.

19. The method of claim 1 further comprising the step of providing a second plurality of photo detector elements onto which is incident the portion of said third coherent beam which is reflected by said beam splitter.

\* \* \* \* \*